US008460398B2

(12) United States Patent
Naoi et al.

(10) Patent No.: US 8,460,398 B2
(45) Date of Patent: Jun. 11, 2013

(54) TWO-PART HAIR DYE

(75) Inventors: Yuki Naoi, Sumida-ku (JP); Yoshinori Saito, Chuo-ku (JP); Toshio Ogawa, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/509,735

(22) PCT Filed: Nov. 30, 2010

(86) PCT No.: PCT/JP2010/071303
§ 371 (c)(1), (2), (4) Date: May 14, 2012

(87) PCT Pub. No.: WO2011/065550
PCT Pub. Date: Jun. 3, 2011

(65) Prior Publication Data

US 2012/0284932 A1 Nov. 15, 2012

(30) Foreign Application Priority Data

Nov. 30, 2009 (JP) ................................ 2009-272812

(51) Int. Cl.
*A61Q 5/10* (2006.01)

(52) U.S. Cl.
USPC ................ 8/405; 8/406; 8/421; 8/435; 8/611; 8/102; 8/111

(58) Field of Classification Search
USPC .............. 8/405, 406, 421, 435, 611, 102, 111
See application file for complete search history.

(56) References Cited

U.S. PATENT DOCUMENTS

| | | | | |
|---|---|---|---|---|
| 6,916,432 | B2 | 7/2005 | Matsuo et al. | |
| 8,153,108 | B2 * | 4/2012 | Fujinuma et al. | ............... 424/62 |
| 2002/0139957 | A1 | 10/2002 | Matsuo et al. | |
| 2004/0213752 | A1 | 10/2004 | Fujinuma et al. | |
| 2010/0316583 | A1 | 12/2010 | Fujinuma et al. | |

FOREIGN PATENT DOCUMENTS

| | | |
|---|---|---|
| CN | 1237410 A | 12/1999 |
| JP | 6 271435 | 9/1994 |
| JP | 2002 226340 | 8/2002 |
| JP | 2002 284655 | 10/2002 |
| JP | 2004 131510 | 4/2004 |
| JP | 2004 339216 | 12/2004 |
| JP | 2007 291015 | 11/2007 |

OTHER PUBLICATIONS

International Search Report Issued Feb. 22, 2011 in PCT/JP10/71303 Filed Nov. 30, 2010.
Office Action issued Feb. 8, 2013, in Chinese Patent Application No. 201080054120.X.

* cited by examiner

*Primary Examiner* — Eisa Elhilo
(74) *Attorney, Agent, or Firm* — Oblon, Spivak, McClelland, Maier & Neustadt, L.L.P.

(57) ABSTRACT

A two-part hair dye including a first part containing an alkali agent, a second part containing hydrogen peroxide, and a non-aerosol foamer container; wherein a liquid mixture contains Components (A) and (B) specified below, wherein the content of hydrogen peroxide in the liquid mixture is 3.60 mass % or higher, and the viscosity of the liquid mixture is 1 to 300 mPa·s. A method for dying hair, wherein a foam of the liquid mixture of the first part and the second part of the two-part hair dye is applied to hair, left to stand for 3 to 60 minutes, and then washed out. Component (A): oxidation dye; Component (B): 0.50 to 3.0 mass %, of polypropylene glycol having a weight-average molecular weight of 200 to 800.

8 Claims, No Drawings

TWO-PART HAIR DYE

FIELD OF THE INVENTION

The present invention relates to a two-part hair dye.

BACKGROUND OF THE INVENTION

Conventionally, a two-part hair bleach and a two-part hair dye have been widely available in the form of liquid or cream for a long time. However, it is difficult for users who are not accustomed to using such a product to evenly apply it to the hair. This is because the viscosity of a mixture to be applied to the hair is adjusted relatively high (for example, approximately 1000 to 10000 mPa·s) for prevention of dripping while the mixture is left on the hair. This makes it difficult to evenly spread the mixture and to adequately cover the hair root with the mixture. Furthermore, skills such as blocking and two-mirror technique are necessary for application of the mixture to the hair root and the back of the head, also requiring much time.

In contrast, a non-aerosol type foamer container discharging a liquid mixture of a two-part hair bleach or a two-part hair dye contained therein in the form of foam is proposed (Patent Document 1). The above hair bleach or hair dye is characterized in that a liquid mixture of the first part and the second part is discharged from a non-aerosol type foamer container in the form of foam, whereby the liquid mixture is evenly applied to the hair even in the case of beginner's use, resulting in an evenly-colored finish. Since it can be easily applied, special skills such as blocking and two-mirror technique is not necessary, and also, time required for hair dyeing can be considerably shortened. As described above, because the above hair bleach or hair dye exhibits far better performance than conventional products, it has come to be common to a wide range of customers, regardless of sex or age. Accordingly, various products have been developed to meet the wide range of customers' needs.

To produce a product for dyeing hair to a light color, a product with a higher concentration of hydrogen peroxide in a liquid mixture is necessary to be formulated. In the development of a formulation containing hydrogen peroxide at a high concentration, the present inventors have come to focus attention on the phenomenon that the liquid temperature of a liquid mixture, under certain conditions, significantly increases within 10 to 20 minutes from immediately after the mixing, the time duration being required for application of the liquid mixture to hair. Such an increase of temperature of the liquid mixture brings disorder to fineness of foam discharged from a foamer container, to easiness of application due to, for example, imbalance of the gas-liquid mixing ratio resulting to watery foam. Further, difference of dyeing power between a dye immediately after the mixing and a dye at 20 minutes after the mixing may be the result of excessively rapid reaction of an oxidation dye, which results to color unevenness. Such a phenomenon has not been observed in liquid or creamy hair dyes which have been conventionally and widely used.

The present inventors have investigated the reason of increase of the temperature of the liquid mixture, and found out that the reason is extremely low viscosity of the hair dye discharged from a non-aerosol foamer container in the form of foam compared to a conventional hair dye, leading to excessively rapid reaction rate of the oxidation dye.

Accordingly, the present inventors have attempted to increase the amount of a higher alcohol in order to improve foam qualities (for example, fineness of foam discharged from a non-aerosol foamer container and proper gas-liquid mixing ratio), even at high liquid temperature. However, it has been reported that a mere use of a higher alcohol may affect the foaming properties at a low temperature (Patent Document 2).

Prior Art Documents

Patent Documents

[Patent Document 1] JP-A-2004-339216

[Patent Document 2] JP-A-2007-291015

SUMMARY OF THE INVENTION

The present invention provides a two-part hair dye which contains a first part containing an alkali agent, a second part containing hydrogen peroxide, and a non-aerosol foamer container for discharging the liquid mixture of the first part and the second part in the form of foam, wherein the liquid mixture contains the following components (A) and (B), wherein the content of the hydrogen peroxide in the liquid mixture is 3.60 mass % or higher, and wherein the viscosity at 25° C. of liquid mixture is 1 to 300 mPa·s.

Component (A): oxidation dye

Component (B): 0.50 to 3.0 mass % of polypropylene glycol having a weight-average molecular weight of 200 to 800.

Further, the present invention provides a method for dying hair, wherein a foam of the liquid mixture of the first part and the second part of the two-part hair dye is applied to hair, left to stand for 3 to 60 minutes, and then washed out.

DETAILED DESCRIPTION OF THE INVENTION

The present invention relates to a two-part hair dye, which provide preferable foam qualities (for example, fineness of discharged foam and a proper gas-liquid mixing ratio) even when the temperature of the liquid mixture of a non-aerosol two-part hair dye increases rapidly due to an oxidation reaction of an oxidation dye, and preferable foaming properties at a low temperature (around 15° C. supposed as room temperature in winter); as well as provides basic performance required as a hair dye and effects characteristic to a non-aerosol two-part hair dye.

The present inventors have discovered that a non-aerosol two-part hair dye containing polypropylene glycol with a specific molecular weight range meets the above needs.

[Alkali Agent]

As an alkali agent contained in the first part, for example, ammonia, an alkanolamine such as monoethanolamine, sodium hydroxide, and potassium hydroxide may be used. Further, an ammonium salt, such as ammonium hydrogen carbonate and ammonium chloride, a carbonate, such as potassium carbonate, and sodium hydrogen carbonate, and the like may appropriately be added as a buffer.

The pH of a liquid mixture of the first part and the second part of the two-part hair dye according to the present invention is preferably 8 to 11, and more preferably 9 to 11; and the alkali agent is used while adjusting the pH of the liquid mixture to fall within the above range.

[Hydrogen Peroxide]

From the viewpoint of ability of dying hair to a light color, the content of hydrogen peroxide contained in the second part in a liquid mixture of the first part and the second part is preferably 3.60 mass % or more, more preferably 3.65 mass % or more, and even more preferably 3.70 mass % or more. On the other hand, from the viewpoint of minimizing damage to the hair, the content of hydrogen peroxide in a liquid mixture of the first part and the second part is preferably 8.00 mass % or less, more preferably 7.00 mass % or less, and even more preferably 6.00 mass % or less. Also, the pH of the second part is preferably 2 to 6, more preferably 2.5 to 4 in order to prevent decomposition of hydrogen peroxide.

[(A): Oxidation Dye]

The first part of the two-part hair dye according to the present invention contains an oxidation dye referred to as Component (A). Examples of the oxidation dye include a dye precursor, such as para-phenylenediamine, para-aminophenol, toluene-2,5-diamine, N,N-bis(2-hydroxyethyl)-para-phenylenediamine, 2-(2-hydroxyethyl)-para-phenylenediamine, 4-amino-3-methylphenol, 6-amino-3-methylphenol, ortho-aminophenol, and 1-hydroxyethyl-4,5-diaminopyrazole; and a coupler, such as resorcin, 2-methylresorcin, meta-aminophenol, 5-amino-ortho-cresol, 5-(2-hydroxyethylamino)-2-methylphenol, meta-phenylenediamine, 2,4-diaminophenoxyethanol, and 1-naphthol.

Two or more of the oxidation dyes of Component (A) may be used in combination, and the content thereof in a liquid mixture of the first part and the second part is, preferably 0.10 to 1.8 mass %, more preferably 0.40 to 1.4 mass %, and even more preferably 0.70 to 1.0 mass %, from the viewpoints of storage stability and dyeability.

Among the oxidation dyes, para-aminophenol is an especially important dye for adjusting the color of hair dye, while it causes rapid oxidation reaction to increase the temperature of a liquid mixture. Consequently, the present invention is preferable when para-aminophenol is at least used as Component (A). If para-aminophenol is used in the two-part hair dye according to the present invention, from the viewpoints of storage stability and dyeability, it is preferably contained in an amount in the range of 0.050 to 0.50 mass %, more preferably 0.10 to 0.40 mass %, and even more preferably 0.15 to 0.30 mass % in a liquid mixture of the first part and the second part.

The first part of the two-part hair dye according to the present invention may contain a direct dye in addition to the oxidation dye. Examples of the direct dye include para-nitro-ortho-phenylenediamine, para-nitro-meta-phenylenediamine, basic yellow 87, basic orange 31, basic red 12, basic red 51, basic blue 99, and acid orange 7.

[(B): Polypropylene Glycol]

The polypropylene glycol having a weight-average molecular weight of 200 to 800 of Component (B) is used for improving the foam qualities, such as the fineness of discharged foam and the proper gas-liquid mixing ratio. The polypropylene glycol is preferably contained in the first part for improvement of storage stability even when the concentration of an oxidation dye is high. The weight-average molecular weight of the polypropylene glycol is more preferably 300 to 500. The weight-average molecular weight means herein a weight-average molecular weight measured by gel permeation chromatography (GPC) and converted into polystyrene.

From the viewpoints of improving the foam qualities of a liquid mixture of the first part and the second part and securing preferable application properties to hair, the content of Component (B) in the liquid mixture is 0.50 to 3.0 mass %, preferably 0.80 to 2.5 mass %, and more preferably 1.2 to 2.0 mass %.

[(C): Linear Saturated Aliphatic Alcohol Having 10 to 30 Carbon Atoms]

Component (C), a linear saturated aliphatic alcohol having 10 to 30 carbon atoms, may be contained for providing preferable fineness and gas-liquid mixing ratio of a foam discharged from a foamer container, even when the reaction heat of a liquid mixture of a two-part hair dye according to the present invention increases the temperature; improving the foam retention after discharging; improving an inhibitory effect against dripping during standing still after application to hair; and moreover improving the foaming properties at a low temperature. The carbon number of the linear saturated aliphatic alcohol having 10 to 30 carbon atoms is preferably 12 to 24, and more preferably 14 to 22. Examples of the linear saturated aliphatic alcohol having 10 to 30 carbon atoms of Component (C) include myristyl alcohol, cetyl alcohol, stearyl alcohol, and behenyl alcohol.

Two or more of Component (C) may be used in combination, which may be contained in either or both of the first part and the second part. From the viewpoints of providing preferable fineness and gas-liquid mixing ratio of a foam discharged from a foamer container even when the reaction heat of a liquid mixture increases the temperature, improving the foam retention after discharging, improving an inhibitory effect against dripping during standing still after application to hair, and moreover improving the foaming properties at a low temperature, the content of Component (C) in a liquid mixture of the first part and the second part is preferably 0.50 to 0.85 mass %, more preferably 0.60 to 0.82 mass %, and even more preferably 0.70 to 0.79 mass %.

[Surfactant]

Surfactant may be further added to either one or both of the first part and the second part in order to easily prepare stable foam by mixing of air and a hair cosmetic composition through foam discharging means of a foamer container.

Examples of anionic surfactant include a sulfuric acid ester anionic surfactant such as alkyl sulfate and alkyl ether sulfate; a carboxylic acid anionic surfactant such as an N-acylamino acid salt, an N-acyl-N-alkylamino acid salt, an amide type N-acylamino acid salt, an ether carboxylate, a fatty acid salt, alkyl succinate, and alkenyl succinate; a sulfonic acid anionic surfactant such as sulfosuccinate type, isethionate type, taurine salt type, alkylbenzenesulfonic acid salt type, α-olefin sulfonic acid salt type, and alkanesulfonic acid type; and a phosphoric acid ester anionic surfactant such as alkyl phosphate and alkyl ether phosphate. Among them, carboxylate and sulfate ester surfactants are preferable, and especially carboxylate surfactants are preferable. Among carboxylate anionic surfactants, an N-acylamino acid salt and an ether carboxylate are preferable; and among them an N-acylglutamate, whose acyl group has generally 10 to 18 carbon atoms, preferably 10 to 16 carbon atoms, and more preferably 10 to 14 carbon atoms, and a polyoxyethylene alkyl carboxylate, whose alkyl group has generally 10 to 18 carbon atoms, preferably 10 to 16 carbon atoms, and more preferably 10 to 14 carbon atoms, and whose average addition mole number of oxyethylene groups is 3 to 15, preferably 3 to 12, and more preferably 4 to 10, are preferable.

Examples of the nonionic surfactant include an alkyl polyglucoside, a polyoxyalkylene alkyl ether, and an alkyl glyceryl ether. The alkyl group of the alkyl polyglucoside has preferably 8 to 18 carbon atoms, more preferably 8 to 14 carbon atoms, and even more preferably 9 to 11 carbon atoms, and the alkyl group is preferably linear. The average degree of polymerization of the glucoside is preferably 1 to 5, and more preferably 1 to 2. The alkyl group of the polyoxyalkylene alkyl ether has preferably 10 to 22 carbon atoms, more preferably 12 to 18 carbon atoms, and the alkyl group is preferably linear. Also, the polyoxyethylene alkyl ether is more preferable, and especially the average addition mole number of the oxyethylene group of the polyoxyethylene alkyl ether is preferably 1 to 40, more preferably 4 to 30. The alkyl group of the alkyl glyceryl ether has preferably 8 to 18 carbon atoms, more preferably 8 to 12 carbon atoms, and the alkyl group is preferably branched.

The cationic surfactant is preferably a mono long-chain alkyl quaternary ammonium salt. Specific examples thereof include cetrimonium chloride, steartrimonium chloride, behentrimonium chloride, stearalkonium chloride, and benzalkonium chloride. Among these, steartrimonium chloride and behentrimonium chloride are more preferable. Examples of a commercially available cationic surfactant include QUARTAMIN 86W, QUARTAMIN 86P CONC, QUARTAMIN 60W, and QUARTAMIN D2345P (the products of Kao Corporation), and NIKKOL CA-2580 (the product of Nihon Surfactant Kogyo K.K.).

Examples of the amphoteric surfactant include carbobetaine, amidobetaine, sulfobetaine, hydroxyl sulfobetaine, amidosulfobetaine, phospho-betaine, and imidazolinium surfactants having an alkyl group, an alkenyl group, or an acyl group having 8 to 24 carbon atoms. Among them, a carbobetaine surfactant and a sulfobetaine surfactant are preferable. Preferred examples of the amphoteric surfactant include lauric acid amidopropyl betaine, coconut oil fatty acid amidopropyl betaine, lauryldimethylaminoacetic acid betaine, and laurylhydroxysulfobetaine.

As a surfactant, in order to provide preferable foaming suitable for applying to hair at a low liquid temperature as well as near normal temperature, an anionic surfactant and a nonionic surfactant are preferable. Two or more of the surfactants may be used in combination; and the content thereof in the liquid mixture of the first part and the second part is 2 to 10 mass %, preferably 2.5 to 7 mass %, and more preferably 3 to 5 mass %.

In order to improve the foam qualities at a low liquid temperature, the weight ratio of an anionic surfactant to a nonionic surfactant in the liquid mixture (content of anionic surfactant/content of nonionic surfactant) is preferably 0.01 to 1, and more preferably 0.1 to 0.5.

[Cationic Polymer]

A two-part hair dye according to the present invention may contain a cationic polymer in either or both of the first part and the second part. A cationic polymer means a polymer having a cationic group or a group ionizable to a cationic group, and includes an ampholytic polymer, which can be cationic as a whole. Namely, examples of a cationic polymer include those having an amino group or an ammonium group in a side chain of the polymer chain, or those containing a diallyl quaternary ammonium salt as a constituent unit, such as cationized cellulose, cationic starch, cationized guar gum, a polymer or a copolymer of a diallyl quaternary ammonium salt, and quaternized polyvinylpyrrolidone.

Specific examples of a polymer or a copolymer of a diallyl quaternary ammonium salt include a dimethyl diallyl ammonium chloride polymer (polyquaternium-6, e.g. MERQUAT 100; Nalco Company), a dimethyl diallyl ammonium chloride/acrylic acid copolymer (polyquaternium-22, e.g. MERQUAT 280, ditto 295, by Nalco Company), a dimethyl diallyl ammonium chloride/acrylamide copolymer (polyquaternium-7, e.g. MERQUAT 550; Nalco Company); an acrylic acid/diallyl quaternary ammonium salt/acrylamide copolymer (polyquaternium-39, e.g. MERQUAT Plus 3331; Nalco Company).

Specific examples of quaternized polyvinylpyrrolidone include a quaternary ammonium salt obtained from a copolymer of vinylpyrrolidone (VP) and dimethylaminoethyl methacrylate, and diethyl sulfate (polyquaternium-11, e.g. Gafquat 734, ditto 755, ditto 755N, by ISP Japan Ltd.).

Specific examples of cationized cellulose include a polymer of a quaternary ammonium salt obtained by adding glycidyl trimethylammonium chloride to hydroxyethyl cellulose (polyquaternium-10, e.g. Leoguard G, ditto GP; Lion Corporation; Polymer JR-125, ditto JR-400, ditto JR-30M, ditto LR-400, ditto LR-30M; Amerchol Corporation), and a hydroxyethyl cellulose/dimethyl diallylammonium chloride copolymer (polyquaternium-4, e.g. Cellcoat H-100, ditto L-200, by National Starch and Chemical Co.)

Among them, polymers having a structure of a dimethyl diallylammonium salt as a constituent unit, such as polyquaternium-4, polyquaternium-6, polyquaternium-7, polyquaternium-22, and polyquaternium-39, are preferable, more preferable are polyquaternium-6, polyquaternium-7, polyquaternium-22, and polyquaternium-39, and especially polyquaternium-22 is preferable.

The cationic polymer is preferably water-soluble. Two or more of the cationic polymers may be used in combination, and the content thereof in a liquid mixture of the first part and the second part is, from the viewpoints of preferable foaming, prevention of dripping and preferable discharging properties from a foamer container preferably 0.01 to 3 mass %, more preferably 0.05 to 2 mass %, and even more preferably 0.1 to 1 mass %.

[Other Components]

Additionally, the first part and the second part may contain silicones, a fragrance, an ultraviolet absorber, a chelating agent such as edetic acid, a disinfectant, an antiseptic agent such as methyl para-hydroxybenzoate, phenacetin, 1-hydroxyethane-1,1-diphosphonic acid, a stabilizer such as hydroxyquinoline sulfate, an organic solvent, such as ethanol, benzyl alcohol, and benzyloxyethanol, a polymer such as hydroxyethyl cellulose, and a humectant according to intended use. A liquid mixture of the first part and the second part preferably contains water as a major solvent.

The two-part hair dye according to the present invention is provided as a two-part oxidation hair dye having the first part containing an alkali agent and the second part containing hydrogen peroxide. In this regard, the two-part dye may also include a three-part oxidation hair dye, in which a third part containing a persulfate or a third part containing a conditioning component or the like is further mixed for use in addition to the first part and the second part. The mixing ratio of the first part to the second part is preferably 1:4 to 4:1 by mass, and more preferably 1:3 to 1:2.

[Viscosity]

The viscosity of a liquid mixture of the first part and the second part is 1 to 300 mPa·s, preferably 2 to 200 mPa·s, more preferably 3 to 100 mPa·s, and even more preferable 5 to 30 mPa·s. Herein, the viscosity is a value measured after rotation of the sample for one minute at 60 rpm at 25° C. by a B-type rotational viscometer (TV-10 model) manufactured by Tokyo Keiki Inc. with rotor No. 1 or No. 2. When the sample for measurement is less than 100 mPa·s, the No. 1 rotor is used for measurement, and when 100 to 499 mPa·s, the No. 2 rotor is used. The measurement is conducted in a thermostatic chamber at 25° C., and measured immediately after mixing the first part and the second part, provided that the temperature change by the reaction heat is neglected.

As the viscosity of a liquid mixture of the first part and the second part is adjusted to fall within the aforementioned range, foam volume can be adjusted for easy application, dripping of the liquid mixture applied to the hair can be prevented, and a foam can be easily discharged by squeezing of a squeeze foamer etc. In order to adjust the viscosity of the liquid mixture to fall within aforementioned range, a water-soluble solvent such as ethanol may be added, or the content and the kind of, for example, the surfactant, the polyols, the higher alcohol may be appropriately adjusted or selected.

[Gas-liquid Mixing Ratio]

The gas-liquid mixing ratio of air and the liquid mixture through the foam discharging means of the foamer container is preferably 7 to 40 mL/g, and more preferably 15 to 30 mL/g, from the viewpoint of easily fitting the hair dye for the hair and easy application. The gas-liquid mixing ratio herein is a value measured as follows.

Firstly, the weight and the volume of foam discharged at 25° C. are measured to obtain a gas-liquid mixing ratio. 100 g of the liquid mixture is placed into an S1 squeeze foamer (Daiwa Can Company, 210 mL volume, the coarseness (aperture) of a mesh is, 150 mesh (150 openings per inch (25.4 mm)) in a mixing chamber, and 200 mesh at the discharge outlet). Discharging has initiated and when the amount of remaining liquid mixture has reached 80 g, 20 g of foam is discharged into a 1000 mL graduated cylinder, and the volume of the discharged foam is measured one minute after initiation of discharging. The volume of discharged foam (mL) is divided by a weight of 20 g to obtain a gas-liquid mixing ratio (mL/g).

[Foamer Container]

In the present invention, a foamer container is a non-aerosol type container, which is used for discharging a liquid mixture of the first part and the second part in the form of foam by mixing it with air without using a propellant. The foamer container can effectively prevent spattering of discharged dye. Among these, a non-aerosol type container is preferable because it can be produced at a lower cost than an aerosol type container, and it can be handled more safely during distribution as no high-pressure gas propellant needs to be used.

For example, a publicly-known pump foamer container with foam discharge means, a squeeze foamer container, an electric foamer, an accumulator pump foamer container can be used as the foamer container. Specific examples thereof include pump foamer E3 type, pump foamer F2 type [the products of Daiwa Can Company, “Food & Packaging” (vol. 35, No. 10, pages 588 to 593 (1994); vol. 35, No. 11, pages 624 to 627 (1994); vol. 36, No. 3, pages 154 to 158 (1995))], an S1 squeeze foamer (Daiwa Can Company, JP-A-7-215352), an electric foamer (Matsushita Electric Works, Ltd.), and an air spray foamer (Airspray International, Inc.). As the foamer container to be used for the two-part foam-type hair dye of the present invention, a pump foamer container and a squeeze foamer container are preferable because of low cost and easy handleability.

The pump foamer container or the squeeze foamer container has a foam-forming unit such as a net. The net is preferably a thin net, because the net which is clogged with dried and solidified liquid mixture of the first part and the second part can be cleaned with the next discharged flow of foam to immediately dissolve the solidified liquid mixture. In this case, the mesh of the net is preferably 50 to 280 mesh, more preferably 90 to 250 mesh, and even more preferably 130 to 220 mesh. The “mesh” as unit hereinafter refers to the number of mesh per inch. Use of the net having the mesh within the above range enables formation of creamy foam. Also, the net may be made of, for example, nylon, polyethylene, polypropylene, polyester, Teflon (Registered Trademark), carbon fiber and stainless, more preferably nylon, polyethylene, polypropylene or polyester, and even more preferably nylon.

The foamer container used in the two-part foam-type hair dye of the present invention is generally equipped with at least one sheet of the net, preferably more than one sheets of the net, from the viewpoints of, for example economic efficiency and foam stability, two nets are preferably arranged; one in mixing chamber and the other in discharge outlet.

A part in the foamer container which is in contact with the content (inner wall of the container, the inner wall of the foam discharge means, and the like) is preferably composed of materials which are resistant to corrosion by alkali and hydrogen peroxide and which is permeable to oxygen generated by decomposition of hydrogen peroxide.

Product form of the two-part foam-type hair dye of the present invention composed of the first part, the second part, and the foamer container is not limited; for example, the first part and the second part may be contained in respective containers other than the foamer container, and they may be transferred to the foamer container and mixed upon application. Alternatively, one of the parts may be contained in the foamer container while the other may be contained in another container, and the part in the another container may be transferred to the foamer container upon application. In this case, the second part is preferably contained in a gas-permeable container, especially in a foamer container composed of an oxygen-permeable material (for example, polyethylene) for prevention of increase of pressure inside the container due to oxygen generated by decomposition of hydrogen peroxide. Meanwhile, a container which is hardly permeable to oxygen is preferably used for the first part, for prevention of oxidation of the oxidation dye.

[Method of Application]

The hair is preferably combed before dyeing the hair (particularly, head hair) with the two-part foam-type hair dye of the present invention. This step is effective for prevention of splattering of the liquid mixture because the hair is not tangled during the re-foaming treatment to be described below after the combing. After combing the hair, blocking treatment which is usual for application of hair dye composition is not necessary. Furthermore, blocking treatment is preferably not applied, in order to make the below-described step of application of a hair dye composition to the hair and re-foaming step easy. Subsequently, the first part and the second part of the two-part hair dye of the present invention are mixed in the foamer container. The liquid mixture discharged in the form of a foam from the container may be applied to the hair directly or using a tool such as hands or a brush. From the viewpoint of prevention of splattering and dripping of the dye, the foam is preferably discharged in (gloved) hands first, and then applied to the hair.

After application, the hair dye is left to stand on the hair for approximately 3 to 60 minutes, preferably approximately 5 to 45 minutes. The hair dye is preferably re-foamed on the hair during the leaving to stand in order to prevent dripping more effectively while the hair dye is left on the hair and to adequately cover the hair root with the liquid mixture. The re-foaming may be performed by, for example, gas injection, using a tool such as vibrator and a brush or fingers, preferably by fingers.

The re-foaming step may be performed after complete disappearance of the foam, during disappearance of the foam, or before change of the applied foam. Alternatively, the re-foaming step may be performed after completion of application of the foam to the entire areas for application of the hair dye, or may be performed during application. The re-foaming step may be performed continuously once or intermittently repeated for several times.

After these steps, the liquid mixture is rinsed off. Subsequently, the hair is appropriately washed with shampoo, treated with conditioner, and then rinsed with water, followed by drying.

EXAMPLE

Examples 1 to 9, Comparative Examples 1 to 6

The first part and the second part formulated as shown in Tables 1 to 3 (mass %) were prepared and charged into respective containers, and the room temperature was set to 25° C. and the liquid temperature was set to 25° C. The first part and the second part were mixed at a mixing ratio (mass ratio) of 1:2 in a squeeze foamer (manufactured by Daiwa Can Company, 210 mL volume, 150 mesh at mixing chamber and 200 mesh at discharge outlet, 0.35 $mm^2$ at the narrowest opening area of an air induction passage, and 1.7 mm inner diameter of a dip tube), and the resulting liquid mixture was discharged from the squeeze foamer.

The following items were evaluated by five expert panelists according to the following criteria and the mean values are shown in Tables 1 to 3 below the table showing formulation.

Quality of Foam Discharged at 25° C.

The first part and the second part maintained in atmosphere of 25° C. for 1 hour or longer were charged into a single container, and 60 seconds after the charging (the time period is assumed to be a practical time period required before starting hair dyeing process) the content was discharged from a squeeze foamer; and the foam qualities were evaluated according to the following criteria.

5: Excellent shape retention, and fine foam
4: Good shape retention, and fine foam
3: Slightly loose, or slightly coarse foam
2: Loose, or coarse foam
1: Watery foam, or coarse foam with a lot of large bubble Property When Discharging at 15° C.

The first part and the second part kept at 15° C. for 1 hour or longer were charged into a single container, and 60 seconds after the charging (the time period is assumed to be a practical time period required before starting hair dyeing process) the content was discharged from a squeeze foamer; and the squeezability was evaluated according to the following criteria.

5: Excellently easy to squeeze
4: Easy to squeeze
3: Average
2: Slightly hard to squeeze
1: Hard to squeeze Quality of Foam Discharged at 15° C.

The first part and the second part kept at 15° C. for 1 hour or longer were charged into a single container, and 60 seconds after the charging (the time period is assumed to be a practical time period required before starting hair dyeing process) the content was discharged from a squeeze foamer; and the foam qualities were evaluated according to the following criteria.

5: Excellent shape retention, and fine foam
4: Good shape retention, and fine foam
3: Slightly loose, or slightly coarse foam
2: Loose, or coarse foam
1: Watery foam, or coarse foam with a lot of large bubble Quality of Foam Discharged at 35° C.

The first part and the second part kept at 35° C. for 1 hour or longer were charged into a single container, and 60 seconds after the charging (the time period required for mixing uniformly) the content was discharged from a squeeze foamer; and the foam qualities were evaluated according to the following criteria.

5: Good shape retention, and strong foam
4: Slightly loose foam
3: Loose foam
2: Remarkably loose foam
1: Liquid form, not foamy Hair Dyeability 1 g of foam discharged at 25° C. was applied with pressing by hand to a Chinese white hair tress BM-W (A) manufactured by Beaulax Co., Ltd. (10 cm, 1 g) in order to coat the tress uniformly. After being left standing for 20 minutes, the tress was gently washed with water, shampooed, and dried; and the color difference before and after hair dyeing ($\Delta E$) was determined.

Dyeing Levelness 70 g of foam discharged at 25° C. was applied with pressing by hand to a wig with hair cut at the chin level (No. 755s, Beaulax Co., Ltd., total hair weight approx. 70 g) in order to coat the wig uniformly. After being left standing for 20 minutes, the wig was gently washed with water, shampooed, and dried. The dyeing levelness was evaluated according to the following criteria.

5: No color unevenness, excellently uniform dyeing
4: Almost no color unevenness, uniform dyeing
3: Average
2: Slightly recognizable color unevenness
1: Severe color unevenness Property when Application Simultaneous with the evaluation of the dyeing levelness as above, easiness of application of the foam was evaluated according to the following criteria.

5: The hair was fully, up to the roots, coated with the foam by gently pressing the foam by hand
4: The hair was easily, up to the roots, coated with the foam by hand combing
3: Average
2: Some parts of the hair, for example hair roots of the dense occipital hair, was difficult to be coated with the foam
1: Insufficient coating, some parts of the hair, e.g. hair roots, remain uncoated Lightness 1 g of foam discharged at 25° C. was applied with pressing by hand to a Chinese black hair tress BS-B (A), manufactured by Beaulax Co., Ltd. (10 cm, 1 g) in order to coat the tress uniformly. After being left standing for 20 minutes, the tress was gently washed with water, shampooed, and dried; and the lightness L* was determined.

TABLE 1

| First part:second part = 1:2 (mass ratio) | | Example | | | | |
|---|---|---|---|---|---|---|
| (The content values are active amounts in the respective parts.) | | 1 | 2 | 3 | 4 | 5 |
| First part | (A): para-aminophenol | 0.8 | 0.8 | 0.8 | 0.8 | 0.8 |
| | (A): toluene-2,5-diamine | 0.8 | 0.8 | 0.8 | 0.8 | 0.8 |
| | (A): 5-amino-ortho-cresol | 0.5 | 0.5 | 0.5 | 0.5 | 0.5 |
| | (A): resorcin | 0.9 | 0.9 | 0.9 | 0.9 | 0.9 |
| | (B): polypropylene glycol (weight-average molecular weight of 400) | 4.0 | — | 2.0 | 7.0 | 4.0 |
| | (B): polypropylene glycol (weight-average molecular weight of 700) | — | 4.0 | — | — | — |
| | (B)': polypropylene glycol with molecular weight of 1000 | — | — | — | — | — |

TABLE 1-continued

| First part:second part = 1:2 (mass ratio) | | Example | | | | |
|---|---|---|---|---|---|---|
| (The content values are active amounts in the respective parts.) | | 1 | 2 | 3 | 4 | 5 |
| | (B)': polyethylene glycol with molecular weight of 300 | — | — | — | — | — |
| | (B)': dipropylene glycol (molecular weight of 134) | — | — | — | — | — |
| | ammonium hydrogencarbonate | 9.6 | 9.6 | 9.6 | 9.6 | 9.6 |
| | ammonia | 2.0 | 2.0 | 2.0 | 2.0 | 2.0 |
| | monoethanolamine | 2.4 | 2.4 | 2.4 | 2.4 | 2.4 |
| | sodium polyoxyethylene(5) lauryl ether acetate | 3.5 | 3.5 | 3.5 | 3.5 | 3.5 |
| | sodium cocoylglutamate | 7.2 | 7.2 | 7.2 | 7.2 | 7.2 |
| | alkyl (8 to 16) glucoside | 1.2 | 1.2 | 1.2 | 1.2 | 1.2 |
| | polyoxyethylene(23) lauryl ether | 2.0 | 2.0 | 2.0 | 2.0 | 2.0 |
| | polyoxyethylene(9) tridecyl ether | 0.5 | 0.5 | 0.5 | 0.5 | 0.5 |
| | ethanol | 10.0 | 10.0 | 10.0 | 10.0 | 10.0 |
| | dimethyl diallylammonium chloride/acrylic acid copolymer* | 1.44 | 1.44 | 1.44 | 1.44 | 1.44 |
| | ascorbic acid | 0.4 | 0.4 | 0.4 | 0.4 | 0.4 |
| | tetrasodium edetate dihydrate | 0.1 | 0.1 | 0.1 | 0.1 | 0.1 |
| | anhydrous sodium sulfite | 0.5 | 0.5 | 0.5 | 0.5 | 0.5 |
| | purified water | balance | balance | balance | balance | balance |
| Second part | cetanol | 0.88 | 0.88 | 0.88 | 0.88 | 0.64 |
| | myristyl alcohol | 0.253 | 0.253 | 0.253 | 0.253 | 0.18 |
| | hydrogen peroxide | 5.7 | 5.7 | 5.7 | 5.7 | 5.7 |
| | stearyl trimethylammonium chloride | 0.84 | 0.84 | 0.84 | 0.84 | 0.84 |
| | polyoxyethylene(40) cetyl ether | 0.55 | 0.55 | 0.55 | 0.55 | 0.55 |
| | hydroxyethanediphosphonic acid | 0.04 | 0.04 | 0.04 | 0.04 | 0.04 |
| | hydroxyquinoline(2) sulfate | 0.04 | 0.04 | 0.04 | 0.04 | 0.04 |
| | sodium hydroxide | 0.016 | 0.016 | 0.016 | 0.016 | 0.016 |
| | purified water | balance | balance | balance | balance | balance |
| Evaluation | Quality of foam discharged at 25° C. | 5.0 | 5.0 | 5.0 | 4.8 | 4.6 |
| | Property when Discharging at 15° C. | 4.4 | 4.4 | 4.2 | 4.4 | 4.6 |
| | Quality of foam discharged at 15° C. | 4.2 | 4.2 | 4.2 | 4.4 | 4.4 |
| | Quality of foam discharged at 35° C. | 4.4 | 4.2 | 4.4 | 4.2 | 4.0 |
| | Hair dyeability (ΔE) | 44 | 45 | 44 | 44 | 45 |
| | Dyeing levelness | 5.0 | 5.0 | 5.0 | 5.0 | 5.0 |
| | Property when Application | 5.0 | 5.0 | 5.0 | 5.0 | 5.0 |
| | Lightness (L*) | 14 | 14 | 15 | 15 | 15 |

*MERQUAT 295 (Nalco Company)

TABLE 2

| First part:second part = 1:2 (mass ratio) | | Example | | | |
|---|---|---|---|---|---|
| (The content values are active amounts in the respective parts.) | | 6 | 7 | 8 | 9 |
| First part | (A): para-aminophenol | 0.18 | 0.4 | 0.8 | 1.2 |
| | (A): toluene-2,5-diamine | 0.8 | 0.4 | 2.0 | 0.8 |
| | (A): 5-amino-ortho-cresol | 0.5 | 0.25 | 0.8 | 0.5 |
| | (A): resorcin | 0.9 | 0.45 | 0.9 | 0.9 |
| | (B): polypropylene glycol (weight-average molecular weight of 400) | 4.0 | 4.0 | 4.0 | 4.0 |
| | (B): polypropylene glycol (weight-average molecular weight of 700) | — | — | — | — |
| | (B)': polypropylene glycol with molecular weight of 1000 | — | — | — | — |
| | (B)': polyethylene glycol with molecular weight of 300 | — | — | — | — |
| | (B)': dipropylene glycol (molecular weight of 134) | — | — | — | — |
| | ammonium hydrogen carbonate | 9.6 | 9.6 | 9.6 | 9.6 |
| | ammonia | 2.0 | 2.0 | 2.0 | 2.0 |
| | monoethanolamine | 2.4 | 2.4 | 2.4 | 2.4 |
| | sodium polyoxyethylene(5) lauryl ether acetate | 3.5 | 3.5 | 3.5 | 3.5 |
| | sodium cocoylglutamate | 7.2 | 7.2 | 7.2 | 7.2 |
| | alkyl (8 to 16) glucoside | 1.2 | 1.2 | 1.2 | 1.2 |
| | polyoxyethylene(23) lauryl ether | 2.0 | 2.0 | 2.0 | 2.0 |
| | polyoxyethylene(9) tridecyl ether | 0.5 | 0.5 | 0.5 | 0.5 |
| | ethanol | 10.0 | 10.0 | 10.0 | 10.0 |
| | dimethyl diallylammonium chloride/acrylic acid copolymer* | 1.44 | 1.44 | 1.44 | 1.44 |
| | ascorbic acid | 0.4 | 0.4 | 0.4 | 0.4 |
| | tetrasodium edetate dihydrate | 0.1 | 0.1 | 0.1 | 0.1 |
| | anhydrous sodium sulfite | 0.5 | 0.5 | 0.5 | 0.5 |
| | purified water | balance | balance | balance | balance |
| Second part | cetanol | 0.88 | 0.88 | 0.88 | 0.88 |
| | myristyl alcohol | 0.253 | 0.253 | 0.253 | 0.253 |
| | hydrogen peroxide | 5.7 | 5.7 | 5.7 | 5.7 |
| | stearyl trimethylammonium chloride | 0.84 | 0.84 | 0.84 | 0.84 |
| | polyoxyethylene(40) cetyl ether | 0.55 | 0.55 | 0.55 | 0.55 |
| | hydroxyethanediphosphonic acid | 0.04 | 0.04 | 0.04 | 0.04 |
| | hydroxyquinoline (2) sulfate | 0.04 | 0.04 | 0.04 | 0.04 |
| | sodium hydroxide | 0.016 | 0.016 | 0.016 | 0.016 |
| | purified water | balance | balance | balance | balance |

TABLE 2-continued

| | First part:second part = 1:2 (mass ratio) (The content values are active amounts in the respective parts.) | Example 6 | 7 | 8 | 9 |
|---|---|---|---|---|---|
| Evaluation | Quality of foam discharged at 25° C. | 4.8 | 4.6 | 4.6 | 4.8 |
| | Property when Discharging at 15° C. | 4.4 | 4.4 | 4.4 | 4.4 |
| | Quality of foam discharged at 15° C. | 4.0 | 4.0 | 4.2 | 4.2 |
| | Quality of foam discharged at 35° C. | 4.4 | 4.4 | 4.2 | 4.0 |
| | Dyeing levelness | 5.0 | 5.0 | 5.0 | 5.0 |
| | Property when Application | 5.0 | 5.0 | 4.8 | 5.0 |

*MERQUAT 295 (Nalco Company)

TABLE 3

| | First part:second part = 1:2 (mass ratio) (The content values are active amounts in the respective parts.) | Comparative Exampe 1 | 2 | 3 | 4 | 5 | 6 |
|---|---|---|---|---|---|---|---|
| First part | (A): para-aminophenol | 0.8 | 0.8 | 0.8 | 0.8 | 0.8 | — |
| | (A): toluene-2,5-diamine | 0.8 | 0.8 | 0.8 | 0.8 | 0.8 | — |
| | (A): 5-amino-ortho-cresol | 0.5 | 0.5 | 0.5 | 0.5 | 0.5 | — |
| | (A): resorcin | 0.9 | 0.9 | 0.9 | 0.9 | 0.9 | — |
| | (B): polypropylene glycol (weight-average molecular weight of 400) | 1.0 | 10.0 | — | — | — | 4.0 |
| | (B)': polypropylene glycol with molecular weight of 1000 | — | — | 1.0 | — | — | — |
| | (B)': polyethylene glycol with molecular weight of 300 | — | — | — | 4.0 | — | — |
| | (B)': dipropylene glycol (molecular weight of 134) | — | — | — | — | 4.0 | — |
| | ammonium hydrogen carbonate | 9.6 | 9.6 | 9.6 | 9.6 | 9.6 | 9.6 |
| | ammonia | 2.0 | 2.0 | 2.0 | 2.0 | 2.0 | 2.0 |
| | monoethanolamine | 2.4 | 2.4 | 2.4 | 2.4 | 2.4 | 2.4 |
| | sodium polyoxyethylene(5) lauryl ether acetate | 3.5 | 3.5 | 3.5 | 3.5 | 3.5 | 3.5 |
| | sodium cocoylglutamate | 7.2 | 7.2 | 7.2 | 7.2 | 7.2 | 7.2 |
| | alkyl (8 to 16) glucoside | 1.2 | 1.2 | 1.2 | 1.2 | 1.2 | 1.2 |
| | polyoxyethylene(23) lauryl ether | 2.0 | 2.0 | 2.0 | 2.0 | 2.0 | 2.0 |
| | polyoxyethylene(9) tridecyl ether | 0.5 | 0.5 | 0.5 | 0.5 | 0.5 | 0.5 |
| | ethanol | 10.0 | 10.0 | 10.0 | 10.0 | 10.0 | 10.0 |
| | dimethyl diallylammonium chloride/acrylic acid copolymer* | 1.44 | 1.44 | 1.44 | 1.44 | 1.44 | 1.44 |
| | ascorbic acid | 0.4 | 0.4 | 0.4 | 0.4 | 0.4 | 0.4 |
| | tetrasodium edetate dihydrate | 0.1 | 0.1 | 0.1 | 0.1 | 0.1 | 0.1 |
| | anhydrous sodium sulfite | 0.5 | 0.5 | 0.5 | 0.5 | 0.5 | 0.5 |
| | purified water | balance | balance | balance | balance | balance | balance |
| Second part | cetanol | 0.88 | 0.88 | 0.88 | 0.88 | 0.88 | 0.88 |
| | myristyl alcohol | 0.253 | 0.253 | 0.253 | 0.253 | 0.253 | 0.253 |
| | hydrogen peroxide | 5.7 | 5.7 | 5.7 | 5.7 | 5.7 | 5.7 |
| | stearyl trimethylammonium chloride | 0.84 | 0.84 | 0.84 | 0.84 | 0.84 | 0.84 |
| | polyoxyethylene(40) cetyl ether | 0.55 | 0.55 | 0.55 | 0.55 | 0.55 | 0.55 |
| | hydroxyethanediphosphonic acid | 0.04 | 0.04 | 0.04 | 0.04 | 0.04 | 0.04 |
| | hydroxyquinoline(2) sulfate | 0.04 | 0.04 | 0.04 | 0.04 | 0.04 | 0.04 |
| | sodium hydroxide | 0.016 | 0.016 | 0.016 | 0.016 | 0.016 | 0.016 |
| | purified water | balance | balance | balance | balance | balance | balance |
| Evaluation | Quality of foam discharged at 25° C. | 4.0 | 3.4 | 4.0 | 3.8 | 3.8 | 3.6 |
| | Property when Discharging at 15° C. | 1.2 | 4.4 | 1.4 | 1.2 | 1.2 | 3.2 |
| | Quality of foam discharged at 15° C. | 1.2 | 4.4 | 1.4 | 1.2 | 1.2 | 3.2 |
| | Quality of foam discharged at 35° C. | 4.4 | 2.8 | 4.4 | 4.4 | 4.4 | 4.4 |
| | Hair dyeability (ΔE) | 45 | 44 | 44 | 44 | 44 | — |
| | Dyeing levelness | 4.8 | 4.8 | 5.0 | 5.0 | 5.0 | 5.0 |
| | Property when Application | 4.8 | 3.4 | 4.8 | 4.6 | 4.6 | 4.8 |
| | Lightness (L*) | 14 | 14 | 14 | 14 | 15 | — |

*MERQUAT 295 (Nalco Company)

As shown in the above evaluation results, Examples 1 to 9, in which polypropylene glycol (weight-average molecular weight: 400) was contained in an amount specified according to the present invention, exhibited favorable performance in all the items, although when the content was close to the limit values, the evaluation results were slightly decreased. With respect to hair dyeability and lightness, no performance deterioration was observed.

On the other hand, less preferable results were observed in Comparative Examples 1 to 6. Comparative Example 1, in which the content of polypropylene glycol (weight-average molecular weight: 400) was less than the specified amount, exhibited decreased evaluation in foam qualities and property when discharging at 15° C.; and Comparative Example 2, in which the content was more than the specified amount, exhibited decreased evaluation in foam qualities at 25° C. and 35° C., as well as property when application.

Further, decreased evaluation in foam qualities and property when discharging at 15° C. were observed in the case where polypropylene glycol (weight-average molecular weight: 200 to 800) as Component (B) was substituted with polypropylene glycol (weight-average molecular weight: 1000) (Comparative Example 3), polyethylene glycol (weight-average molecular weight: 300) (Comparative Example 4), and dipropylene glycol (Comparative Example 5).

In the case where an oxidation dye was not contained (Comparative Example 6), preferable evaluation was not observed in foam qualities at 25° C. and 15° C., and property when discharging at 15° C. This is because the formulation of the present invention is based on additional incorporation of an oxidation dye. In another word, reaction heat derived from the oxidation dye is not generated without containing oxidation dye, and consequently the temperature at discharging does not increase, and preferable performance cannot be exhibited by the formulation which is ready for generation of the reaction heat.

The invention claimed is:

1. A two-part hair dye comprising a first part comprising an alkali agent, a second part comprising hydrogen peroxide, and a non-aerosol foamer container for discharging a liquid mixture of the first part and the second part in the form of a foam, wherein the liquid mixture comprises components (A) and (B);

component (A): an oxidation dye component (B): 0.50 to 3.0 mass % of polypropylene glycol having a weight-average molecular weight of 200 to 800, wherein the content of the hydrogen peroxide in the liquid mixture is 3.60 mass % or higher, and wherein a viscosity at 25° C. of the liquid mixture is 1 to 300 mPa·s.

2. The two-part hair dye according to claim 1, further comprising component (C) in the liquid mixture from 0.50 to 0.85 mass %, wherein the component (C) is a linear saturated aliphatic alcohol having 10 to 30 carbon atoms.

3. The two-part hair dye according to claim 1, wherein the oxidation dye comprises 0.050 to 0.50 mass % of para-aminophenol in the liquid mixture.

4. The two-part hair dye according to claim 1, wherein the total content of the Component (A) in the liquid mixture is 0.10 to 1.8 mass %.

5. A method for dyeing hair, comprising applying a liquid mixture of the first part and the second part of the two-part hair dye according to claim 1 in the form of a foam to hair, letting the hair dye to stand for 3 to 60 minutes, and, thereafter, washing the liquid mixture from the hair.

6. The two-part hair dye according to claim 2, wherein the oxidation dye comprises 0.050 to 0.50 mass % of para-aminophenol in the liquid mixture.

7. The two-part hair dye according to claim 2, wherein the total content of the Component (A) in the liquid mixture is 0.10 to 1.8 mass %.

8. The two-part hair dye according to claim 3, wherein the total content of the Component (A) in the liquid mixture is 0.10 to 1.8 mass %.

* * * * *